United States Patent [19]

Danna et al.

[11] Patent Number: 5,018,506

[45] Date of Patent: May 28, 1991

[54] FLUID CONTROLLED BIASED BENDING NECK

[75] Inventors: Dominick Danna; Allan I. Krauter, both of Syracuse; Raymond A. Lia, Auburn, all of N.Y.

[73] Assignee: Welch Allyn, Inc., Skaneateles Falls, N.Y.

[21] Appl. No.: 539,232

[22] Filed: Jun. 18, 1990

[51] Int. Cl.$^5$ ............................................... A61B 1/00
[52] U.S. Cl. ........................................... 128/4; 92/92
[58] Field of Search ................ 128/4, 6; 92/92, 130 B

[56] References Cited

U.S. PATENT DOCUMENTS

| | | | |
|---|---|---|---|
| 4,794,912 | 1/1989 | Lia | 128/4 |
| 4,890,602 | 1/1990 | Hake | 128/4 |
| 4,893,613 | 1/1990 | Hake | 128/4 |

Primary Examiner—William H. Grieb
Attorney, Agent, or Firm—Wall and Roehrig

[57] ABSTRACT

A tubular, fluid-controlled bending neck is provided for an elongated flexible probe, such as a video borescope. An elongated tubular elastomeric bladder is fitted to a proximal connector that fits onto a distal end of the probe insertion tube, and a distal fitting seals the distal end of the bladder. A tubular braid is disposed over the bladder to confine the same and is mechanically attached to the distal fitting and to the proximal connector. The connector provides communication of fluid presure from a controlled fluid pressure source to be interior of the bladder. An elastically bendable, by axially substantially incompressible spine is disposed at the interface between the bladder and the braid. This spine is preferably set or biased to be curved into one bending direction. As fluid pressure is applied to the bladder, the bladder inflates laterally. This shortens the braid on the side away from the spine, thereby bending the neck in the opposite direction. By applying a pressure intermediate between a zero pressure and the pressure required for full bending the bending neck will assume a straight orientation.

10 Claims, 3 Drawing Sheets

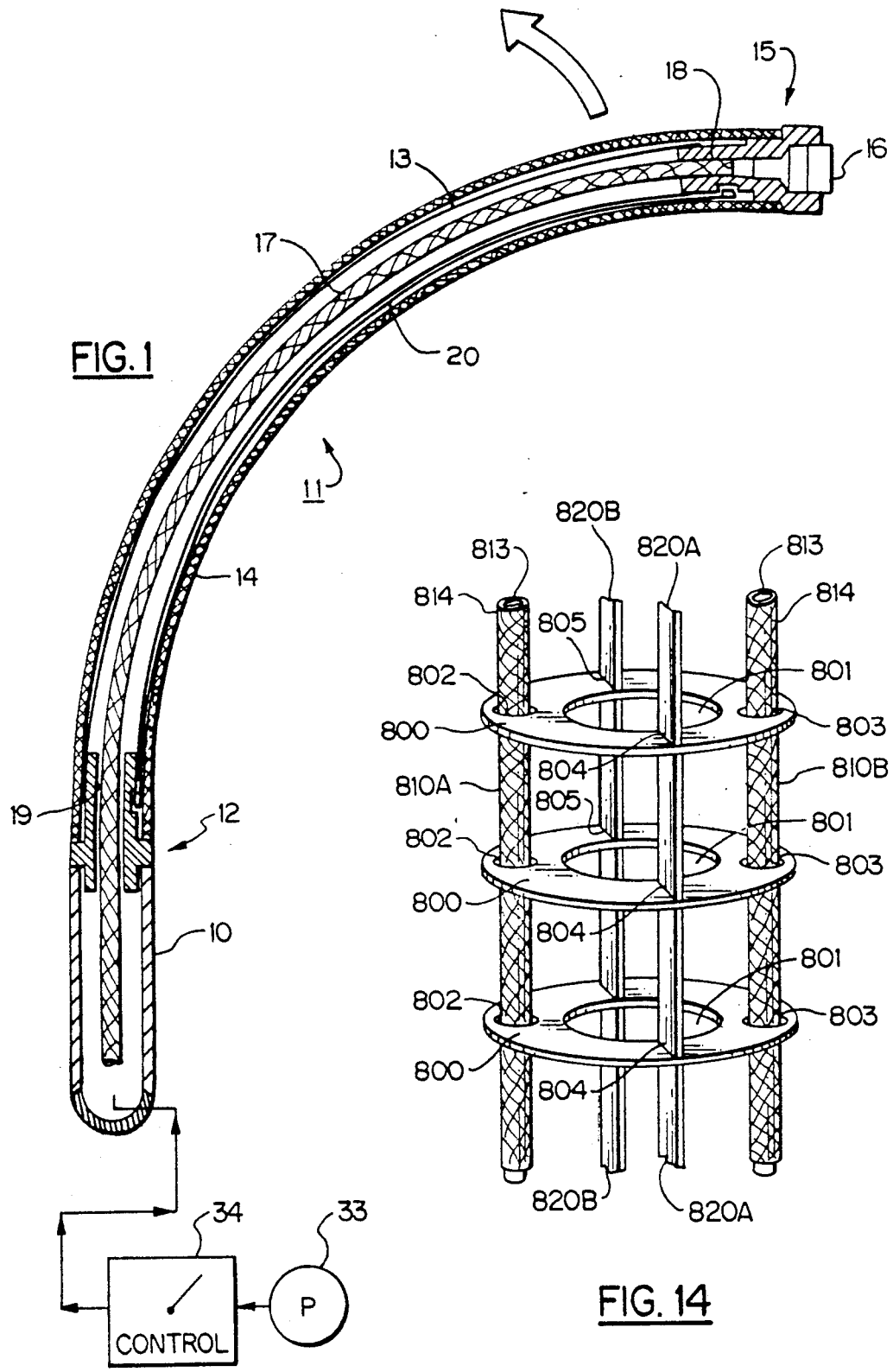

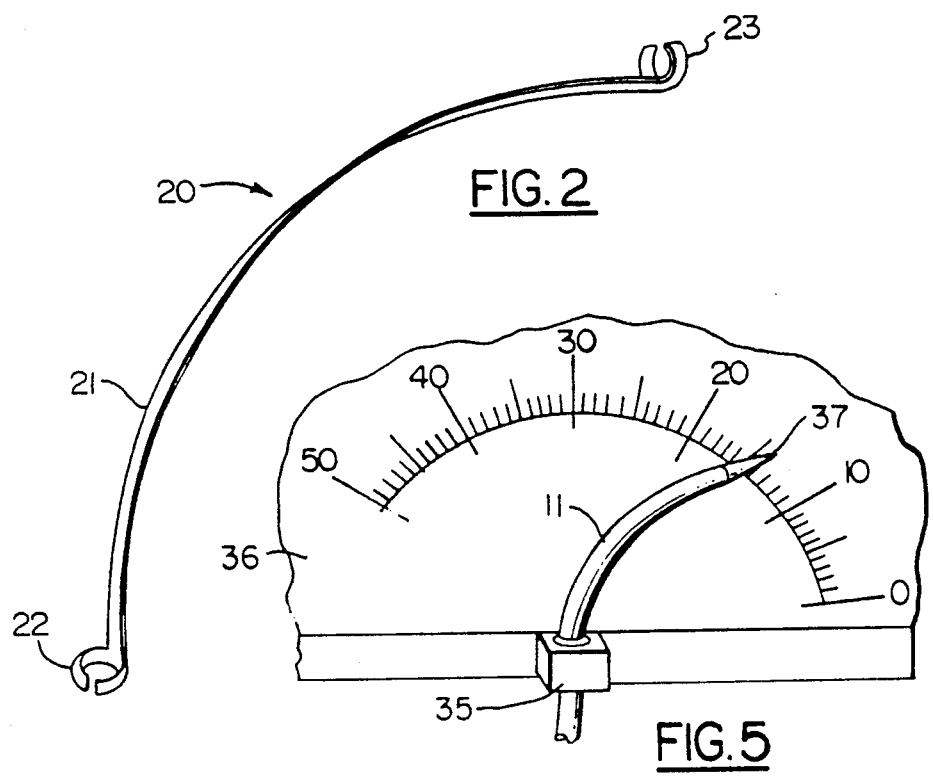
FIG. 2
FIG. 5
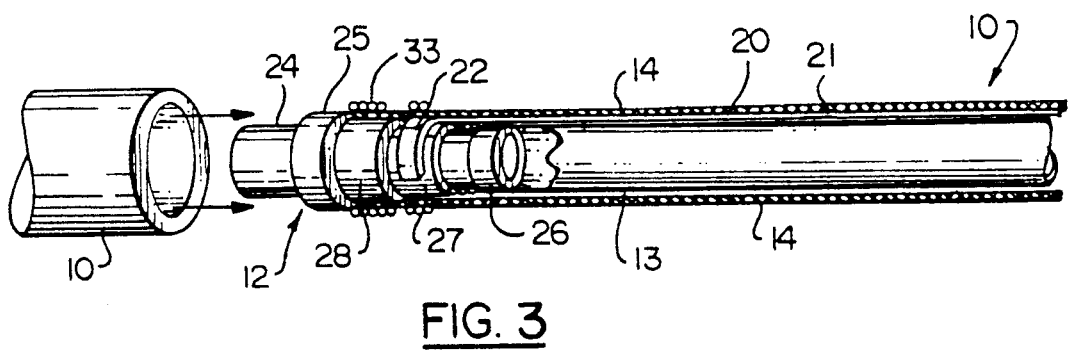
FIG. 3
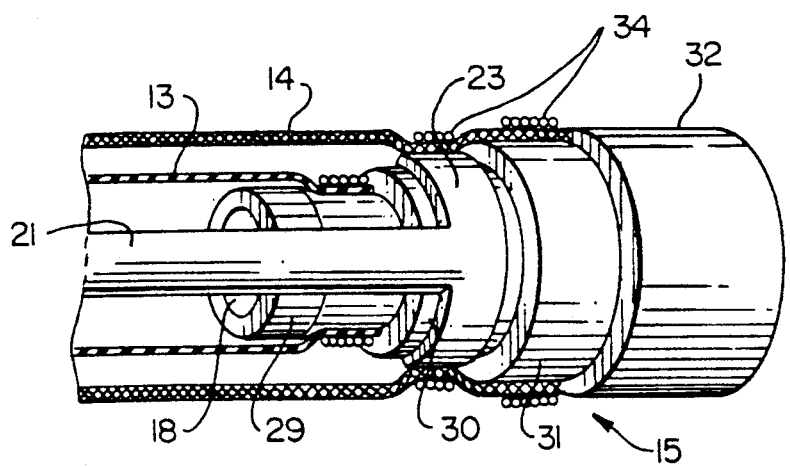
FIG. 4

FLUID CONTROLLED BIASED BENDING NECK

BACKGROUND OF THE INVENTION

This invention relates to fluid actuators, and is more particularly concerned with a device that responds to fluid pressure by bending. This invention is more specifically concerned with a steering section that can be disposed, e.g. at a distal tip of an elongated probe such as a video borescope or optical borescope. However, the invention can be broadly applied to pressure gauges, rotary actuators, and grabbers for remote tools.

A borescope or similar flexible probe can be generally configured as an elongated flexible insertion tube with a viewing head at its distal or forward end and a control housing for controlling or steering the distal or forward end. The typical borescope has a bendable tubular steering section or articulation section at the distal end adjacent the viewing head. The steering section typically comprises a series of alternating wobble washers and spacers, with control cables that extend through the wobble washers and then through the remainder of the flexible insertion tube. The steering cables connect with a steering control unit in the control section. Each such pair of cables is differentially displaced to bend the steering section in a bending plane. In this manner, the viewing head can be remotely oriented to facilitate the inspection of an object. Borescopes are often required to bend in narrow, tortuous passageways, so the radial dimension of the borescope is often quite limited, i.e., 6 mm diameter. Also, the pathway to the object or target can be quite long, which then requires the insertion tube and the steering cables to be rather long, e.g., fifteen feet or more.

A number of cable-actuated articulation or steering mechanisms are known, and typical ones are discussed in U.S. Pat. Nos. 3,610,231; 3,739,770; 3,583,393; 3,669,098; 3,779,151; and 4,347,837. Another steering mechanism is described in U.S. Pat. No. 4,700,693.

These cable-actuated articulation mechanisms require the cables to have a significant amount of slack or play because bends and coils in the insertion tube effectively shorten the cables and because the articulation section bends at discrete points rather than following a smooth arc. However, in many applications the articulation section must bend rather precisely to penetrate the tortuous passages into the area to be inspected without damaging delicate engine parts. For these reasons, cable tension must be limited and cable slack must be minimized. Moreover, where the insertion tube is long, extra cable slack is often included to accommodate the increased cable tightening due to the substantial coiling and bending of the insertion tube through which the steering cables pass.

A proposed arrangement to permit steering cables to be kept short as possible is described in U.S. Pat. No. 4,794,912. That patent described a braid-and-bladder pneumatic or hydraulic "muscle," i.e., linear traction motor, that addresses many of the problems found in these prior-art steering mechanisms. Specifically, fluid dynamic muscles mounted adjacent the distal end of the insertion tube are actuated by pneumatic or hydraulic pressure supplied through small flexible tubes within the borescope insertion tube. Short steering cables connect the respective muscles with the articulation mechanism. As fluid pressure is applied differentially to a pair of muscles, the cables move differentially and the articulation mechanism bends the steering section a desired amount.

While this system avoids many of the above-mentioned problems, especially those associated with extremely long cables, there are residual problems because of the reliance on an otherwise conventional cable steering mechanism. The steering section is rather complex and expensive, and does not follow a natural arc, as mentioned before. Further simplification, by replacing the cable driven steering mechanism, should reduce or eliminate these residual drawbacks, but a suitable alternative steering mechanism has eluded those in the art.

OBJECTS AND SUMMARY OF THE INVENTION

It is an object of this invention to provide a simple, reliable steering mechanism which can be used on an elongated flexible probe.

It is another object of this invention to eliminate cables, wobble washers, and other complex mechanical actuation devices from the steering section for a probe.

According to one aspect of the invention, an articulation or steering assembly has an elongated tubular elastomeric bladder and a tubular braid disposed over the bladder to confine it so that when the bladder is inflated it expands the braid laterally, but shortens it. A distal fitting seals a distal end of the bladder and serves as a point for mechanical attaching to the distal end of the braid. A proximal connector sealably fits the proximal end of the bladder and anchors the proximal end of the braid. A central passage through the connector communicates fluid pressure from a controlled fluid pressure source (either pneumatic or hydraulic) to the interior of the bladder for controllably inflating the same. A resiliently bendable, but axially incompressible spine is disposed between the bladder and the braid and extends along one side of the longitudinal axis of the bending neck. The spine includes clamping sections at its proximal and distal ends for mechanically affixing the spine to the proximal connector and the distal fitting. When fluid pressure is applied to the interior of the bladder, the braid expands laterally and shortens axially on the unsupported side, i.e., on the side away from the spine. This bends the neck a controlled amount that depends on the fluid pressure applied.

Preferably, the spine is biased, or naturally formed in an arc that is bent to the spine side of the bending neck. When the applied pressure is at a zero or threshold pressure, the neck is biased to the one side. When full pressure is applied, the neck is bent arcuately in the opposite direction. At an intermediate pressure, the bending neck is substantially straight. The degree of curvature within the plane of bending is substantially proportional to the applied pressure.

The viewing head, which can be optical or video, can be situated in the distal fitting of the bending neck. A signal conduit or bundle, which can be a wire bundle in the case of a video device or a fiber optic bundle in the case of an optical device, can pass from the head through the distal fitting, then along axis of the bladder, and through a central passage in the proximal connector and thence through the insertion tube to a suitable viewing device. A clearance of the passage with respect to the signal conduit can serve to communicate fluid pressure, through the insertion tube, to the interior of the bladder.

This braid-and-bladder bending neck provides two-way steering (i.e., in a single bending plane) without cables, cable sheaths, or wobble washers. The diameter of the bending neck can be made extremely small, permitting a steerable probe to be constructed of small diameter, e.g. 4 mm. The neck bends substantially along a true arc over its operating range, e.g., from −60 or more to +60 or more degrees of arc.

The above and many other objects, features, and advantages of this invention will become apparent from the ensuing description of a preferred embodiment, which should be read in connection with the accompanying Drawing.

BRIEF DESCRIPTION OF THE DRAWING

FIG. 2 illustrates the spine employed in this embodiment.

FIGS. 3 and 4 are partial assembly views showing the proximal and distal ends of the bending neck, respectively.

FIG. 5 illustrates a simple pressure gauge that embodies the present invention.

DETAILED DESCRIPTION OF THE PREFERRED EMBODIMENT

Figures 1, 14:
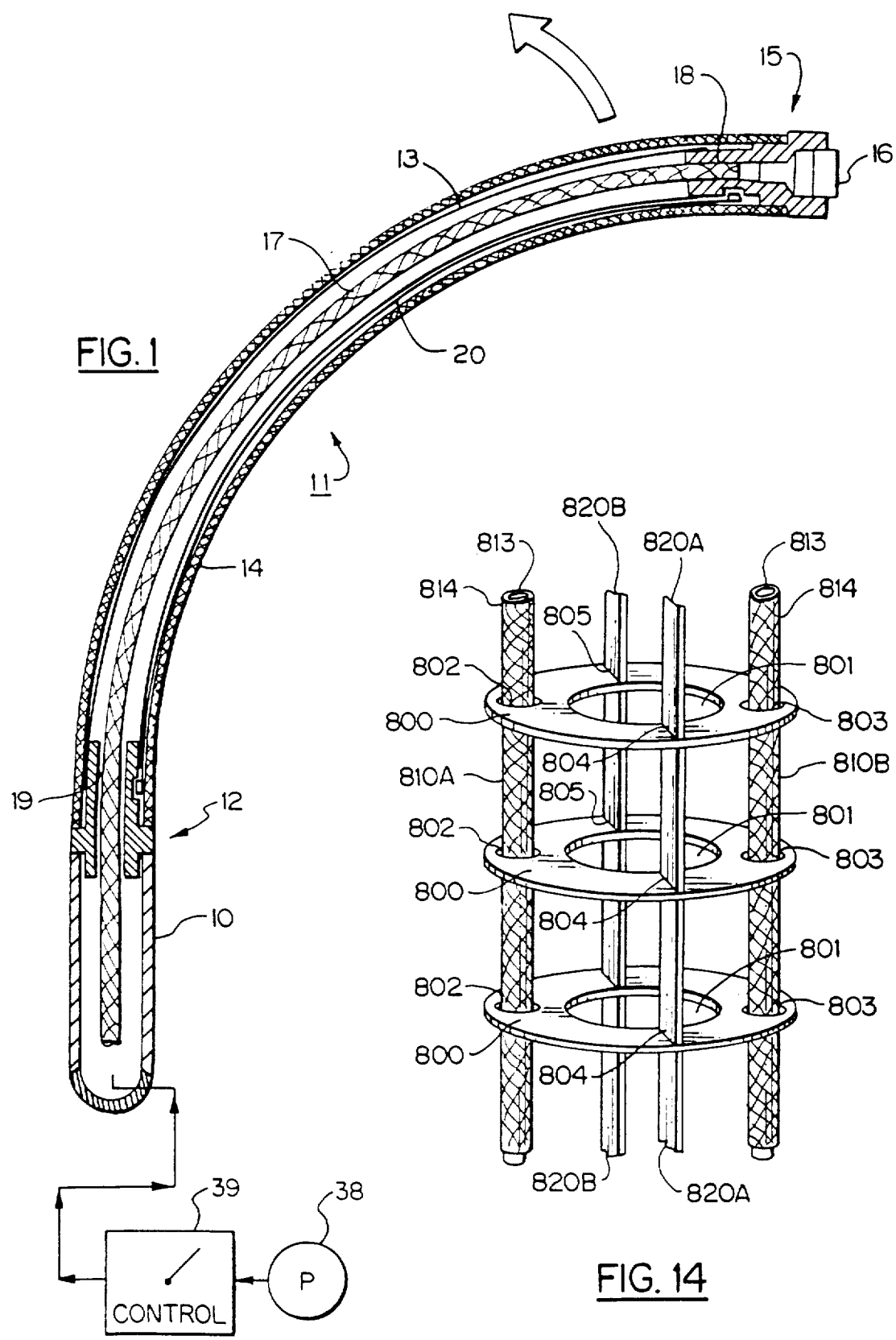
FIG. 1 is a sectional view of a tubular fluid-controlled bending neck according to one embodiment of the present invention.
FIG. 14 is a schematic illustration of a steering mechanism according to a still further embodiment of this invention.

With reference to the Drawing, and initially to FIG. 1 thereof, a small-diameter flexible video probe is shown to include a hollow flexible insertion tube 10, having a bending neck assembly 11 attached onto its distal end. The assembly 11 has a proximal connector 12 that fits into the insertion tube 10 and serves as an attachment point for an elongated tubular elastomeric bladder 13. A braid 14, which is formed of helically wound, substantially inextensible filaments, some of which are right-hand wound and some of which are left-hand wound, surrounds the bladder 13 and has its proximal end attached to the connector 12. A distal fitting 15 seals the distal end of the bladder 13 and is mechanically attached to the distal end of the tubular braid 14. In this embodiment, there is a miniature video camera and optics canister 16 situated in the fitting 15. A signal conduit 17, which contains a wire bundle that carries signals to and from the video canister 16, and also contains a fiber optic bundle for illumination, reaches the canister 16 through a receptacle 18 in the distal fitting 15. The conduit 17 proceeds proximally within the bladder 13 and continues generally along the axis of the bending neck 11 and out through a central passage 19 in the proximal connector 12. From that point, the conduit 17 proceeds through the insertion tube 10 to a control processor and viewer (not shown) located at the proximal end of the insertion tube.

A flexible resilient spine 20 at the interface between the bladder 13 and the braid 14 is disposed at one side of the bending neck 11, i.e. at the right side as shown in FIG. 1. As better illustrated in FIG. 2, the spine 20 has an elongated leaf 21 that is flexible but resists axial contraction. The leaf 21 is arcuately biased, i.e. is set into a curve of a predetermined arc, of e.g. 60°. This leaf 21 is preferably of oblong cross section with the long dimension being disposed along the braid bladder interface. The cross-sectional dimension can typically be 0.100 by 0.005 inches. A generally cylindrical clamp portion 22 is formed at the proximal end and a similar clamp portion 23 is formed at the distal end of the spine 20. These clamp portions attach by interference fit, adhesive, and wraps of cording or monofilament to the connector 12 and fitting 15, respectively.

As shown in FIG. 3, the proximal connector 12 has a generally tubular sleeve 24 that fits into the insertion tube 10, and an annular land 25 that matches the diameter of the insertion tube. Distally of the land 25, a tube barb 26 receives the proximal end of the bladder 13 which can be secured onto it by cement and tied on with a suitable monofilament cord. A first annular step 27 receives the proximal clamp portion 22 of the spine 20, and a second step 28 receives the proximal end of the braid 14, which is secured to it with a suitable cement. Monofilament wraps 33 tie both the proximal clamp 22 and the proximal end of the braid 14 onto the connector 12.

As shown in FIG. 4, the distal end fitting 15 has a tube barb 29 that receives the distal end of the bladder 13, which can be suitably secured and sealed to it with a cement and tied with a coil of monofilament cord. Distally of the tube barb 29, a first annular step 30 receives the distal clamp portion 23 of the spine 20, and another step 31 receives the distal end of the braid 14 which is cemented to it with a suitable cementing compound. Monofilament wraps 34 tie both the distal clamp portion 23 and the distal end of the braid 14 onto the distal end fitting 15. A distal annular land 32 substantially matches the outer diameter of the braid 14.

As indicated in FIG. 1, a source 33 of pressurized fluid, e.g., compressed air, supplies the same through a suitable controllable pressure regulator 34 to the interior of the insertion tube 10. The fluid pressure can be varied accurately over a range, e.g. from 0 to 100 psig. There is a clearance between the interior of the central passage 19 and the signal conduit 17 to permit fluid communication between the interior of the insertion tube 10 and the interior of the bladder 13. When a zero or sub-threshold pressure is applied through the control 34 to the insertion tube 10 and bladder 13, the spine 20 holds the bending neck 11 in its repose position, e.g. bent fully to the right, as shown in FIG. 1. As the pressure is increased, the bladder 13 will inflate, and will expand laterally. The effect of the helical braid 14 is to permit the bladder to expand only by reducing its axial length. However, the braid can shorten only on the side away from the spine 20. Thus, as the pressure increases within the bladder 13, the bending neck 11 bends in the direction of the arrow, i.e. to the left in the drawing. At full pressure, the bending neck 11 is bent in the opposite direction in the bending plane, i.e., 60° or more to the left. To obtain a straight bending neck, an intermediate pressure is applied. For any particular degree of bending, the bending neck 11 assumes a smooth arcuate curve, and is not subject to the segmented bending characteristics of cable-drive articulation mechanisms of the type mentioned previously.

The bending neck 11 can be operated either pneumatically or hydraulically. Because of its simple design, the diameter of the entire mechanism can be kept quite small, permitting construction of an articulatable probe of less than 6 mm diameter. Also, because the air or hydraulic pressure can be accurately controlled, the bending neck 11 can be constructed to operate with negligible play or hysteresis.

An alternative application of this invention is as a pressure gauge, such as illustrated in FIG. 5. Here, a bending neck 11 is supported in a holder 35 so that the bending plane of the neck 11 is parallel to a dial face 36. A pointer 37 at the distal tip of the neck 11 points to a pressure indication on the distal face 36. Adjustment is carried out by moving the neck 11 axially within the holder 35. This arrangement is a simple indicator for either gas or fluid pressure.

Figure 6:
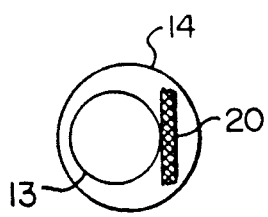
FIG. 6 is a schematic cross sectional view of a biased two-way bending neck of the embodiment of FIGS. 1 to 4.

FIG. 6 is a schematic cross section of the bending neck 11 of the embodiment generally illustrated in FIGS. 1 to 4, showing the bladder 13, braid 14, and spine 20, with the spine 20 at the interface between the braid 14 and bladder 13.

FIGS. 7 to 13 are similar cross sectional views of several alternative embodiments.

Figure 7:
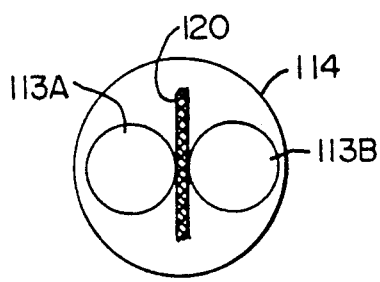

FIG. 7 shows a bending neck for unbiased two-way steering. In this embodiment a spine 120 is flexible, but assumes a straight orientation in the absence of bending forces from a pair of bladders 113A, 113B that are disposed on opposite sides of the spine 120 and within a common tubular braid 114. The bladders are inflated alternately. The spine 120 bends when one of the bladders is inflated, with the inflated bladder being on the inside of the curve. The spine moves away from the inflated bladder during articulation. A differential pressure regulator (not shown) is employed to inflate the bladders 113A, 113B.

Figure 8:
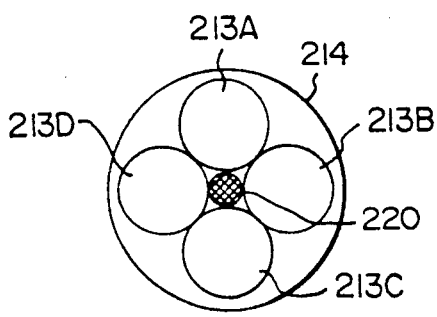

FIG. 8 shows a bending neck arrangement for four-way steering, i.e., left, right, up, and down. Here, a central spine 220 is surrounded by four bladders 213A, 213B, 213C, and 213D arranged in opposed pairs, with a common braid 214. The spine can have round or square cross section, or alternatively can be of regular polygonal cross section. The spine moves away from the inflated bladder during articulation. Opposite bladders are inflated alternately.

Figure 9:
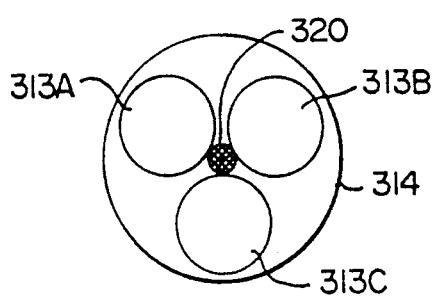

FIG. 9 shows an unbiased three-way bending arrangement, with three bladders 313A, 313B, and 313C disposed at 120 degrees around a central spine 320, all within a common braid 314. The spine 320 moves away from the uninflated bladder or bladders during articulation.

Figure 10:
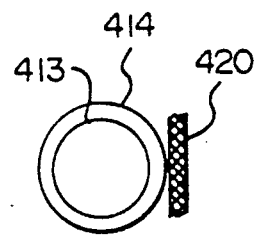
FIGS. 7 to 13 are schematic cross sectional views of alternative embodiments of this invention.

FIG. 10 is an arrangement similar to that of FIG. 6, but in which the spine 420 is disposed outside both the bladder 413 and braid 414. The interface of the braid 414 and spine 420 is bonded at the ends, and if desired along their mutual length.

Figure 11:
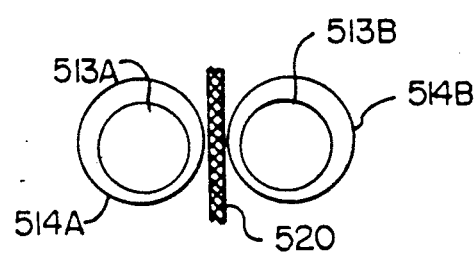

FIG. 11 shows a two-way unbiased bending arrangement with two bladders 513A, 513B, each within its respective braid 514A, 514B, and a spine 520 between the two braids and bonded to them at the ends and/or along their length.

Figure 12:
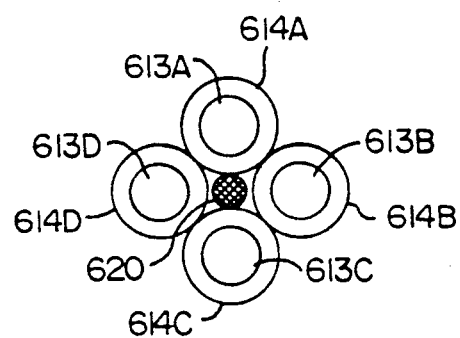
Figure 13:
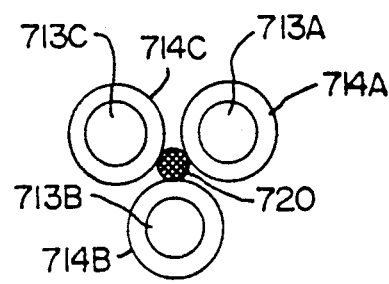

An unbiased four-way steering arrangement is shown in FIG. 12, having four bladders 613A, 613B, 613C, 613D each with its respective braid 614A, 614B, 614C, 614D which are bonded to a central spine 620. FIG. 13 shows a three-way arrangement with three bladders 713A, 713B, 713C and three respective braids 714A, 714B, 714C that are bonded to a central spine 720.

These alternative embodiments are illustrative of many variants that can include a spine and one or more sets of braids and bladder.

FIG. 14 is a schematic view of a two-way articulated steering arrangement according to a further embodiment of the invention. In this arrangement there are a plurality of wobble washers 800, each of which has a central opening 801, a pair of opposite round openings 802, 803, and a pair of opposite slots 804, 805 at ninety degrees from the round openings. A pair of spines 820A, 820B are disposed in the slots and serve as spacers for the wobble washers 800, and define a bending plane as well. A pair of pneumatic or hydraulic muscle assemblies 810A, 810B pass through the round openings 802, 803. Each of the muscles has an elongated elastomeric bladder 813 and a braid 814 over the bladder. The braid can be free to pass through the openings 802, 803 or can be bonded at each wobble washer 800.

Each muscle 810A, 810B is attached to a distal viewing head (not shown) and an anchor point (not shown) proximal of the steering arrangement. With reference to the orientation shown in FIG. 14, when muscle 810A is inflated, the arrangement will bend to the left. When muscle 810B is inflated, the arrangement will bend to the right. When both are deflated, the spines 820A, 820B tend to return the arrangement to a straight orientation.

The central openings 801 align to define a central passageway for wires and optical fibers. In any practical embodiment, a flexible sheath (not shown) would enclose the articulation arrangement.

While not shown, three-way and four-way bending arrangements are also possible, employing the principles of FIG. 11 embodiment.

While this invention has been described in detail with respect to selected preferred embodiments, it should be understood that the invention is not limited to those precise embodiments. Rather, many modifications and variations would present themselves to those of skill in the art without departing from the scope and spirit of this invention as defined in the appended claims.

What is claimed is:

1. A tubular, fluid-controlled bending neck that comprises an elongated tubular elastomeric bladder; a tubular braid disposed over said bladder and confining the same; a distal fitting for sealing the distal end of the bladder and mechanically attaching to the distal end of the braid; a proximal connector to which the proximal end of the bladder is sealably fitted and to which the proximal end of the braid is anchored, including means for communicating fluid pressure from a controlled fluid pressure source to an interior of the bladder for controllably inflating same; and an elastically bendable but substantially axially incompressible spine disposed outside said bladder and adjacent said braid to one side of the longitudinal axis of the bending neck and including means at its proximal and distal ends mechanically fixed to said connector and said fitting, respectively; such that when fluid pressure is applied to the interior of the bladder, the braid expands laterally and shortens axially on the side away from the spine, thereby bending the neck a controlled amount that depends on the fluid pressure applied.

2. The tubular bending neck of claim 1 wherein said spine generally has a cross-section of about 0.100 inches circumferentially and about 0.005 inches radially.

3. The tubular bending neck of claim 1 wherein said spine is arcuately curved to one side of the neck, such that at a zero applied fluid pressure said neck is bent to said one side, at a high fluid pressure said neck is bent to the side away from the spine, and at an intermediate pressure said neck is substantially straight.

4. The tubular bending neck of claim 1 wherein said proximal connector has a central passage through which a flexible bundle passes, said bundle containing electric wires and/or light transmission fibers and continuing axially within the bladder and sealably mating into a receptacle in said distal fitting.

5. The tubular bending neck of claim 4 wherein said passage provides a clearance with respect to said wire bundle.

6. The tubular bending neck of claim 5 wherein said means for communicating fluid pressure to the interior of the bladder includes the clearance through said central passage.

7. A borescope or endoscope which comprises a flexible elongated insertion tube, a viewing head at a distal tip of the insertion tube including illumination fibers and means for collecting a visual image of a target, a flexible signal and illumination conduit within said insertion tube through which light is transmitted to said viewing head and through which image information is transmitted from said viewing head; and a tubular, fluid-controlled bending neck assembly supported on a distal end of said insertion tube and having a distal end supporting said viewing head, comprising an elongated tubular elastomeric bladder; a tubular braid disposed over said bladder and confining same; a distal fitting supporting said viewing head and sealing the distal end of the bladder while mechanically attaching to the distal end of said braid; a proximal connector that connects to the distal end of said insertion tube, to which the proximal end of said bladder is sealably fitted and to which the proximal end of said braid is anchored, said connector including means for communicating fluid pressure from a controlled fluid pressure source to an interior of the bladder for inflating same, and an elastically bendable but axially substantially incompressible spine disposed between said bladder and said braid and extending axially at one side of the longitudinal axis of said bending neck, said spine including means at its proximal and distal ends mechanically affixing the spine to said connector and said fitting, respectively; such that when fluid pressure is applied to the interior of the bladder, the braid expands laterally and shortens axially on the side away from the spine, thereby bending the neck a controlled amount that depends on the fluid pressure applied.

8. The borescope or endoscope of claim 7 wherein said connector has a central axial passage therethrough, and said signal and illumination conduit passes through said bladder, and sealably fits a receptacle in said distal fitting.

9. The borescope or endoscope of claim 8 wherein fluid pressure is applied through said insertion tube and said passage of said connector to the interior of said bladder.

10. The borescope or endoscope of claim 7 wherein said spine is arcuately biased to said one side of the neck so that at a zero applied pressure said neck is bent to said one side, at a high pressure said neck is bent to the side away from said spine, and at an intermediate pressure said neck is substantially straight.

* * * * *

UNITED STATES PATENT AND TRADEMARK OFFICE
CERTIFICATE OF CORRECTION

PATENT NO. : 5,018,506
DATED : May 28, 1991
INVENTOR(S) : Danna et al.

It is certified that error appears in the above—identified patent and that said Letters Patent is hereby corrected as shown below:

The title page, showing the illustrative figure, should be deleted and substitute therefore the attached title page.

Sheet 1 of the drawings, consisting of Figs. 1 and 14, should be deleted to be replaced with the sheet of drawings, consisting of Fig.s 1 and 14, as shown on the attached page.

Column 4, line 35, please change "33" to --38-- and
line 37, please change "34' to --39--.

Signed and Sealed this

Twenty-eighth Day of September, 1993

Attest:

BRUCE LEHMAN

Attesting Officer

Commissioner of Patents and Trademarks

United States Patent [19]
Danna et al.

[11] Patent Number: 5,018,506
[45] Date of Patent: May 28, 1991

[54] FLUID CONTROLLED BIASED BENDING NECK

[75] Inventors: Dominick Danna; Allan I. Krauter, both of Syracuse; Raymond A. Lia, Auburn, all of N.Y.

[73] Assignee: Welch Allyn, Inc., Skaneateles Falls, N.Y.

[21] Appl. No.: 539,232

[22] Filed: Jun. 18, 1990

[51] Int. Cl.⁵ ............................................. A61B 1/00
[52] U.S. Cl. ............................................. 128/4; 92/92
[58] Field of Search ................. 128/4, 6; 92/92, 130 B

[56] References Cited

U.S. PATENT DOCUMENTS

| | | | |
|---|---|---|---|
| 4,794,912 | 1/1989 | Lia | 128/4 |
| 4,890,602 | 1/1990 | Hake | 128/4 |
| 4,893,613 | 1/1990 | Hake | 128/4 |

Primary Examiner—William H. Grieb
Attorney, Agent, or Firm—Wall and Roehrig

[57] ABSTRACT

A tubular, fluid-controlled bending neck is provided for an elongated flexible probe, such as a video borescope. An elongated tubular elastomeric bladder is fitted to a proximal connector that fits onto a distal end of the probe insertion tube, and a distal fitting seals the distal end of the bladder. A tubular braid is disposed over the bladder to confine the same and is mechanically attached to the distal fitting and to the proximal connector. The connector provides communication of fluid presure from a controlled fluid pressure source to be interior of the bladder. An elastically bendable, by axially substantially incompressible spine is disposed at the interface between the bladder and the braid. This spine is preferably set or biased to be curved into one bending direction. As fluid pressure is applied to the bladder, the bladder inflates laterally. This shortens the braid on the side away from the spine, thereby bending the neck in the opposite direction. By applying a pressure intermediate between a zero pressure and the pressure required for full bending the bending neck will assume a straight orientation.

10 Claims, 3 Drawing Sheets

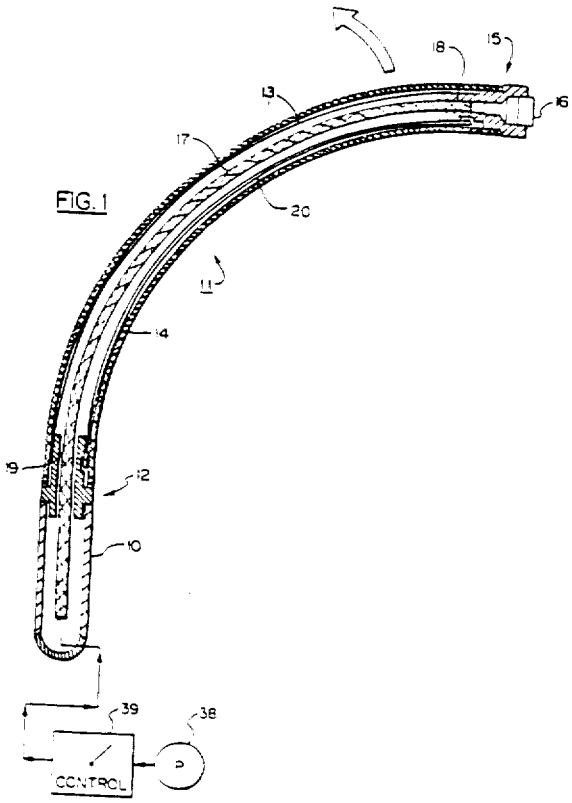

FIG. 1